US005798313A

United States Patent [19]

Carroll et al.

[11] Patent Number: 5,798,313
[45] Date of Patent: Aug. 25, 1998

[54] HETEROGENEOUS CATALYST REGENERATION

[75] Inventors: Kevin M. Carroll, Havertown; Edrick Morales; Yuan-Zhang Han, both of West Chester, all of Pa.

[73] Assignee: ARCO Chemical Technology, L.P., Greenville, Del.

[21] Appl. No.: 770,822

[22] Filed: Dec. 20, 1996

[51] Int. Cl.[6] .................. B01J 20/34; B01J 38/02; B01J 38/12
[52] U.S. Cl. .................. 502/38; 502/56
[58] Field of Search .................. 502/38, 56

[56] References Cited

U.S. PATENT DOCUMENTS

| | | | |
|---|---|---|---|
| 3,923,843 | 12/1975 | Wulff | 260/348.5 L |
| 4,021,454 | 5/1977 | Wulff et al. | 260/348.5 L |
| 4,367,342 | 1/1983 | Wulff et al. | 549/529 |
| 4,876,372 | 10/1989 | Nakanishi et al. | 549/529 |
| 5,011,953 | 4/1991 | Nakanishi et al. | 549/529 |

FOREIGN PATENT DOCUMENTS

| | | |
|---|---|---|
| 0129814 | 6/1984 | European Pat. Off. . |
| 0345856 | 12/1989 | European Pat. Off. . |
| 0734764 | 2/1996 | European Pat. Off. ......... B01J 21/06 |
| 0734764 | 3/1996 | European Pat. Off. . |
| 9609117 | 3/1996 | WIPO . |

OTHER PUBLICATIONS

Yen, *Propylene Oxide & Ethylene Oxide*, Report No. 2C, Apr. 1977, Process Eco. Program (Stanford Research Int) p. 223.

Wang, *Propylene Oxide* Report No. 2E, Aug. 1994, Process Economics Program (SRI International) pp. 6–28.

Yen, *Propylene Oxide & Ethylene Oxide*, Report No. 2C Apr. 1977, Process Economics Program (Stanford Research Int) p. 221.

Cativiela et al., *J. Molecular Catalysis A: Chemical* 112 pp. 259–267 (1996) no month.

*Primary Examiner*—Michael L. Lewis
*Assistant Examiner*—Alexander G. Ghyka
*Attorney, Agent, or Firm*—Stephen D. Harper

[57] ABSTRACT

The activity of titanium-containing heterogeneous catalysts such as titania-on-silica which have been used to catalyze olefin epoxidation is effectively restored by heating in the presence of oxygen at a temperature of 700° C. or greater. Epoxide selectivity is enhanced by treatment of the heated catalyst with a silylating agent, even where the used catalyst had been silylated when initially prepared.

16 Claims, No Drawings

HETEROGENEOUS CATALYST REGENERATION

FIELD OF THE INVENTION

This invention relates to a method of restoring the activity of a titanium-containing supported catalyst which has been used to catalyze an oxidation reaction such as the epoxidation of an olefin with an organic hydroperoxide. Regeneration is accomplished by heating the spent heterogeneous catalyst in the presence of a gas stream comprised of oxygen. It has unexpectedly been discovered that the catalyst must be heated at a temperature of at least 700°0 C. in order to restore catalytic activity to a level comparable to that of fresh catalyst.

BACKGROUND OF THE INVENTION

U.S. Pat. No. 4,367,342 discloses an olefin epoxidation process wherein an olefin is contacted with an organic hydroperoxide in the presence of an insoluble catalyst comprised of an inorganic oxygen compound of titanium. The patent further discloses that at the conclusion of the reaction, the resulting product mixture may be separated and the products recovered by conventional methods such as fractional distillation, selective extraction, filtration and the like. The patent further teaches that the catalyst may be recycled for further utilization. Unfortunately, heterogeneous catalysts of the type disclosed in U.S. Pat. No. 4,367,342, for reasons which are not fully understood, tend to slowly deteriorate in performance when used repeatedly or in a continuous process for a prolonged period of time. In particular, the activity of the catalyst (as measured by the amount of olefin or organic hydroperoxide converted per pass or in a given period of time) decreases with time to a point where continued use of the catalyst charge no longer becomes economically viable. Due to the relatively high cost of synthesizing this type of catalyst, regeneration of the used catalyst would be greatly preferred over replacement.

It has previously been proposed that satisfactory regeneration might be achieved by blowing with hot air to burn away the impurities on the catalyst. However, heating the used catalyst at temperatures typically utilized for regeneration of other heterogeneous catalysts (e.g., zeolites) and sufficient to reduce the catalyst impurities to negligible levels does not significantly improve the activity of the titanium-containing catalysts described hereinabove. For example, heating a spent catalyst at 500° C. burns off essentially all of the organic impurities on the catalyst, yet does not adequately restore catalytic activity. In view of this, a more effective means of regenerating such catalysts is needed.

SUMMARY OF THE INVENTION

The invention provides a method of regenerating a used non-zeolitic heterogeneous catalyst composition comprised of an inorganic oxygen compound of silicon in chemical combination with an inorganic oxygen compound of titanium. Said method comprises heating the used non-zeolitic heterogeneous catalyst composition at a temperature of at least 700° C. in the presence of a gas stream comprised of oxygen to produce a reactivated heterogeneous catalyst composition. Further improvement in catalyst performance is realized by treatment of the heated catalyst with a silylating agent.

DETAILED DESCRIPTION OF THE INVENTION

The catalysts regenerable by practice of the present invention are characterized as heterogeneous, that is, essentially insoluble in an oxidation reaction mixture, and non-zeolitic. Such catalyst compositions comprise an inorganic oxygen compound of silicon in chemical combination with an inorganic oxygen compound of titanium (e.g., an oxide or hydroxide of titanium). The inorganic oxygen compound of titanium is preferably combined with the oxygen compound of silicon in a high positive oxidation state, e.g., tetravalent titanium. The proportion of the inorganic oxygen compound of titanium contained in the catalyst composition can be varied, but generally the catalyst composition contains, based on total catalyst composition, at least 0.1% by weight of titanium with amounts from about 0.2% by weight to about 50% by weight being preferred and amounts from about 0.2% to about 10% by weight being most preferred.

Catalysts of this type are well-known in the art and are described, for example, in U.S. Pat. Nos. 4,367,342, 4,021,454, 3,829,392 and 3,923,843, European Patent Publication Nos. 0129814, 0345856, 0492697 and 0734764, Japanese Kokai No. 77-07,980 (Chem. Abstracts 87:135000s), PCT Application No. WO 94/23834, German Patent Document No. 3,205,648, and Castillo et al., *J. Catalysis* 161, pp. 524–529 (1996), the teachings of which are incorporated herein by reference in their entirety.

The inorganic oxygen compound of silicon is an inorganic siliceous solid containing a major proportion of silica. Amorphous (i.e., non-crystalline) silicon compounds are particularly preferred for use. In general, suitable inorganic siliceous solids are further characterized by having a relatively large surface area in relation to their mass. The term used herein and one normally used in the art to express the relationship of surface area to mass is "specific surface area". Numerically, specific surface area will be expressed as square meters per gram ($m^2/g$). Generally, the inorganic siliceous solid has a specific surface area of at least 1 $m^2/g$ and preferably the average specific surface area is from 25 $m^2/g$ to 800$^2/g$.

Suitable inorganic siliceous solids include synthetic porous silicas consisting of particles of amorphous silica flocculated or linked together so that they form relatively dense, close-packed masses. Representatives of such materials are silica gel and precipitated silica. These silica products are porous, in that they have numerous pores, voids, or interstices throughout their structures.

Other suitable inorganic siliceous solids include synthetic silica powders consisting of particles of amorphous silica flocculated in open-packed, readily disintegrated, loosely knit aggregates. Illustrative silica powders include fumed, pyrogenic silicas obtained by the combustion of hydrogen and oxygen with silicon tetrachloride or tetrafluoride.

Synthetic inorganic oxide materials containing a major proportion of silica comprise another class of inorganic siliceous solids. Such materials are known as refractory oxides and includes silica-alumina, silica-magnesia, silica-zirconia, silica-alumina-boric and silica-alumina-magnesia.

Particularly preferred synthetic inorganic siliceous solids are those consisting essentially of pure silica, e.g., materials containing at least 90% silica.

The preparation of the catalyst may be accomplished by a variety of techniques known in the art. One such method involves impregnating an inorganic siliceous solid support with a titanium tetrahalide (e.g., $TiCl_4$), either by solution or vapor phase impregnation, followed by drying and then calcination at an elevated temperature (e.g., 500° C. to 900° C.). Vapor phase impregnation is described in detail in European Patent Pub. No. 0345856 (incorporated herein by reference in its entirety). In another technique, the catalyst composition is suitably prepared by calcining a mixture of inorganic siliceous solids and titanium dioxide at elevated temperature, e.g., 500° C. to 1000° C. Alternatively, the catalyst composition is prepared by cogelling a mixture of a titanium salt and a silica sol by conventional methods of preparing metal supported catalyst compositions. In still another technique, the catalyst composition is prepared by the surface reaction of silanol groups of an inorganic siliceous solid with a titanium salt by the procedure disclosed in U.S. Pat. No. 3,166,542 of Orzechowski and McKenzie, issued Jan. 19, 1965, U.S. Pat. No. 3,220,959 of Orzechowski, issued Nov. 30, 1965 or U.S. Pat. No. 3,274,120 of Aftandilian, issued Sep. 20, 1966. The catalyst composition is also suitably prepared by the reaction of hydroxyl groups of titanium dioxide containing such groups with a silicon tetrahalide using the same surface reaction procedure disclosed in the above patents. In yet another technique, a catalyst composition comprising a fumed, pyrogenic titania-silica is prepared by the combustion of hydrogen and oxygen with a mixture of silicon tetrahalide and titanium halide in accordance with conventional methods of preparing finely-divided fumed metal oxides and silica. An alternative method involves grafting various amount of titania over the hydroxylated surface of an inorganic siliceous solid using a titanium tetraalkoxide. Other techniques for incorporating an oxide or hydroxide of titanium on an inorganic siliceous-solid such as dry-mixing, co-precipitation, impregnation and ion-exchange are also suitably employed.

One class of heterogeneous catalyst particularly suitable for reactivation using the methods described herein is titania-on-silica (also sometimes referred to as "$TiO_2/SiO_2$"), which comprises titanium (titanium dioxide) supported on silica (silicon dioxide). The titania-on-silica may be in either silylated or nonsilylated form.

The catalyst composition is optionally, and preferably, subject to a pretreatment or activation prior to utilization in an oxidation process. The precise method of pretreatment will depend in part upon the form of chemical combination in which the components are provided, but in general the pretreatment comprises heating an initially prepared catalyst in an atmosphere of a non-reducing gas such as nitrogen, argon, carbon monoxide or preferably, an oxygen-containing gas, e.g., air. One function served by this type of pretreatment operation is to convert the catalyst components into the form of inorganic oxygen compounds if these components are not initially provided in these forms. For example, residual halide or alkoxy groups attached to silica or titanium atoms may be replaced by oxygen or hydroxy groups. Temperatures from about 350° to about 800° C. are generally satisfactory for such purpose. Typical pretreatment times are from about 1 to 18 hours. Subsequent to pretreatment, the titanium catalyst is employed in any convenient physical form, for example, as powder, flakes, spheres or pellets.

Any titanium-halide bonds remaining after calcination may be hydrolyzed. Hydrolysis may be effected with steam at an elevated temperature, preferably in the range of from 150° C. to 400° C.

Another pretreatment method which may be utilized is to treat the catalyst with an organic silylating agent at elevated temperature. Such methods are well-known in the art and are described for example, in U.S. Pat. Nos. 3829,392 and 3,923,843 (incorporated hereby by reference in their entirety). Suitable silylating agents include organosilanes, organosilylamines and organosilazanes. Silylation is typically performed after heating the catalyst at an elevated temperature (e.g., after calcination).

The aforedescribed heterogeneous catalyst compositions are typically utilized in oxidation reactions and are particularly useful for catalyzing the epoxidation of olefins using organic hydroperoxides. Olefin epoxidations of this type are well-known in the art and are described, for example, in U.S. Pat. No. 4,367,342 (incorporated herein by reference in its entirety).

As the olefin reactant in this process may be employed any organic compound having at least one aliphatic olefinically unsaturated carbon-carbon double bond, generally containing from 2 to 30 carbon atoms, but preferably from 3 to 10 carbon atoms. Especially for use are linear alpha olefins of 3 to 10 carbon atoms such as propylene, 1-butene, 1-pentene, 1-octene, and 1-decene.

The hydrocarbon used to prepare the organic hydroperoxide should contain at least one secondary or tertiary carbon atom (i.e., a tetra-substituted carbon atom wherein one or two of the substituents are hydrogen atoms and the remaining substituents are hydrocarbyl). Preferred hydrocarbons include $C_4$–$C_{20}$ aliphatic hydrocarbons, $C_7$–$C_{20}$ aralkyl hydrocarbons and mixtures thereof. Specific illustrative hydrocarbons include isobutane, ethyl benzene, cyclohexane, isopentane, 2-methyl pentane, methyl cyclohexane, tetrahydronaphthalene, cumene, diethyl benzene, 3-methyl pentane, and the like.

The organic hydroperoxide reactants used are secondary or tertiary hydroperoxides, including alkyl hydroperoxides and aralkyl hydroperoxides, wherein a hydroperoxy group is substituted for a hydrogen atom in the starting hydrocarbon. Suitable organic hydroperoxides thus include tertiary butyl hydroperoxide, tertiary amyl hydroperoxide, tertiary hexyl hydroperoxide, tertiary octyl hydroperoxide, ethyl benzene hydroperoxide, tetralin hydroperoxide, cumene hydroperoxide, cyclohexyl hydroperoxide, methyl cyclohexyl hydroperoxide, alpha-ethyl benzyl hydroperoxide, alpha-alpha diethyl benzyl hydroperoxide, and diisopropylene benzene hydroperoxide.

In the epoxidation reaction, the molar ratio of olefin reactant to hydroperoxide can vary over a wide range and a molar excess of either the olefin reactant or hydroperoxide of up to as high as 100:1 can be used. In general, molar ratios of olefin reactant to hydroperoxide varying from about 50:1 to about 1:10 are satisfactory, although it is preferred to employ molar ratios of olefin reactant to hydroperoxide of about 20:1 to about 1:1.

The organic hydroperoxide may be supplied in dilute or concentrated form, with the organic hydroperoxide generally being present in the crude oxidation product and the purified oxidation product at a concentration of about 5 to 70 percent by weight. The crude oxidation product is prepared by direct oxidation methods, such methods being well-known in the art. For example, molecular oxygen may be passed through the hydrocarbon to convert a portion of the hydrocarbon to the corresponding organic hydroperoxide. Such processes are described, for example, in U.S. Pat. Nos. 2,845,461, 3,351,635, 3,459,810, 3,475,498, 2,867,666, 3,351,635, 3,459,810, 3,475,498 and 4,966,706, all of which are incorporated herein by reference in their entirety.

Typically, the hydrocarbon oxidation is carried out in the absence of catalyst at a temperature of about 100° C. to 200° C. and 10 to 500 psia for an amount of time sufficient to achieve the desired degree of conversion. Either pure oxygen, air, or oxygen combined with an inert gas such as nitrogen can be used. Preferably, the hydrocarbon conversion is in the range of 1 to 50%, with the range of 5 to 20% being preferred where the hydrocarbon is ethylbenzene.

The epoxidation is conducted in the liquid phase in solvents or diluents which are liquid at reaction temperature and pressure and are substantially inert to the reactants and the products produced thereof from. Particularly preferred solvents are the hydrocarbons employed for producing the organic hydroperoxide reactants, e.g., alkylbenzenes such as ethylbenzene and isopropylbenzene and tertiary alkanes (an alkane containing a carbon atom attached to a hydrogen atom and 3 other carbon atoms) such as isobutane and isohexane. In certain modifications of the epoxidation process, a portion of the olefin reactant serves as the reaction solvent and no added solvent is needed. In most instances, however, added solvent is used. Amounts up to about 20 moles of solvent per mole of organic hydroperoxide are satisfactory. The process is preferably conducted in an inert reaction environment so that the present of reactive materials such as water is desirably avoided. Suitable reaction conditions are therefore substantially anhydrous.

The epoxidation reaction is suitably conducted by any of a variety of procedures. In one modification, the entire amounts of reactants, the catalyst and the solvent are charged to an autoclave or similar pressure reactor and the reaction mixture is maintained with agitation at the selected reaction temperature and pressure for the desired reaction period. In another modification, one reactant is added to the remaining reaction mixture components in increments, as by adding the organic hydroperoxide to a mixture of the olefin reactant, the catalyst and the solvent maintained at the selected reaction temperature and pressure. In yet another modification, reaction is effected in a continuous manner as by contacting the olefin reactant, the hydroperoxide and the solvent during passage through a reaction zone in which the solid catalyst is maintained particulate form either as a slurry, moving bed, fluidized bed, or fixed bed, for example. The reactants may be passed through the catalyst bed, so that the effluent from the reaction zone is essentially free from catalyst. By any modification, the epoxidation process is conducted at moderate temperatures and pressures. Suitable reaction temperatures vary from about 25° C. to about 200° C., but preferably from 50° C. to 150° C. The reaction is preferably conducted at or above atmospheric pressure. The precise pressure is not critical so long as the reaction mixture is maintained substantially in a non-gaseous phase. Typical pressures vary from about 1 atmosphere to about 100 atmospheres. The epoxidation may successfully be carried out in a batch-wise, continuous, or semi-continuous manner.

Obviously, there is no need to utilize the regeneration process of this invention until the epoxidation activity of the catalyst has diminished to an unacceptable level.

Typically, however, it will be economically desirable to reactivate the catalyst when its activity is between 10 and 50 percent of its activity when freshly prepared, as measured by the rate at which a given hydroperoxide reacts with a given olefin. The length of time between the start of epoxidation and the point at which catalyst activity drops to a level where regeneration is to be initiated will be dependent upon many reaction parameters, including the identifies of the olefin, organic hydroperoxide and solvent, the space velocities of the reactants, the reaction temperature and the nature and amount of impurities and other changes in the catalyst associated with deactivation.

The spent titanium-containing catalyst is preferably separated in solid form from any liquid components of the reaction mixture in which it may be present prior to regeneration. For example, where the catalyst has been deployed in the form of a slurry, it may be readily collected by filtration, centrifugation, decantation, or other such mechanical means and then transferred into a vessel which is suitable for carrying out the regeneration. Alternatively, where the catalyst has been used as a fixed bed, the liquid components may be simply drained or pumped away from the spent catalyst and regeneration conducted in the same vessel as the catalytic process. If this embodiment of the regeneration process is practiced, however, the vessel employed should be constructed of materials capable of withstanding the high temperatures encountered during the regeneration. Of course, a fixed bed catalyst could also be transferred to a different vessel for regeneration purposes. It is not, however, necessary to completely dry the recovered catalyst prior to regeneration since any minor amounts of epoxidation reaction solvent, reactants, and the like adsorbed on the catalyst can be readily removed and disposed of during such regeneration. When the epoxidation reaction is carried out in a fixed bed or a continuously agitated bath, the spent catalyst may be washed with the regeneration solvent by supplying the solvent instead of the epoxidation reaction raw materials to the reactor. If so desired, the spent catalyst may be subjected to an initial drying step at a relatively low temperature in order to remove any volatile components present. For example, a gas stream comprised of oxygen, an inert gas, air or a mixture thereof may be passed through a fixed bed of the spent catalyst at a temperature in the range 25° C. to 200° C. The catalyst may also be exposed to subatmospheric pressure in order to facilitate the removal of volatile substances associated with the catalyst. In one embodiment of the invention, the spent catalyst may be washed with a suitable solvent such as water, a $C_1$–$C_{10}$ aliphatic alcohol or the like to remove substances adhering to the catalyst prior to drying and subsequent high temperature calcination. Washing in this manner helps to remove residual sodium which, if left in the catalyst, may promote collapse of the pore structure of the catalyst at the regeneration temperatures required by the regeneration process.

The spent titanium-containing catalyst is heated in the presence of molecular oxygen at a temperature of at least 700° C., but preferably less than 1000° C. The temperature range of from 750° C. to 900° C. is especially suitable. The spent catalyst may additionally be subjected to temperatures less than 700° C, provided that during at least a portion of the regeneration cycle it is exposed to temperatures of 700° C. or higher. In one embodiment of the invention, the gas containing oxygen is passed over the spent catalyst while the temperature (which initially may be at a relatively low temperature) is slowly elevated to a final temperature in excess of 700° C. The temperature may be kept constant during regeneration or may be periodically or continuously increased or decreased as may be desired. The molecular oxygen may be combined with other gases such as nitrogen and the like; the use of air is especially advantageous due to the low cost and availability of this source of oxygen. The percent molecular oxygen in the gas stream should be selected so that excessive or uncontrollable exotherms are not produced. Typically, the gas stream will comprise from about 1 to 30 volume percent oxygen. The process may be conducted such that a gas stream comprising molecular oxygen is passed over the titanium-containing catalyst in order to sweep away any volatile products evolved from the catalyst. Gas flow rates of 1 to 25 liters per kilogram of catalyst per minute have proven satisfactory. Alternatively, the regeneration may be performed in a static manner. The catalyst could also be agitated or stirred while being contacted with the oxygen-containing gas. In yet another variation of the process, the spent catalyst may be first heated to 700° C. or higher in the absence of oxygen to convert the organic impurities on the catalyst to carbon, then exposed to oxygen to burn off the carbon. The catalyst is heated for such time as may be necessary to restore the desired level of activity and selectivity. Typical heating times are from 0.5 to 48 hours, although a surprising feature of this invention is that catalytic activity comparable to that of fresh catalyst can be restored in 10 hours or less. The optimum time will vary somewhat depending upon the extent to which the catalyst has been deactivated, the type of reaction in which the catalyst, as well as other factors, but may be readily ascertained by routine experimentation. The residence time at a temperature of 700° C. or higher is preferably selected so that the regenerated catalyst catalyzes olefin epoxidation at a rate at least 25%, more preferably at least 50%, greater than that of the untreated catalyst.

Following heat treatment, the regenerated catalyst may be further treated if so desired prior to reuse in an oxidation reaction to further modify its catalytic properties. A particularly desirable additional treatment involves reacting the heated catalyst with a silylating agent. Illustrative silylating agents include organosilanes, organosilylamines, and organosilazanes. Organosilanes containing from one to three organic substituents may be utilized, including, for example, chlorotrimethylsilane, dichlorodimethyl silane, nitrotrimethylsilane, chlorotriethylsilane, chlorodimethylphenylsilane and the like. Preferred organohalosilane silylating agents include tetrasubstituted silanes having from 1 to 3 halo substituents selected from chlorine, bromine, and iodine with the remainder of the substituents being methyl, ethyl or a combination thereof. Organodisilazanes are represented by the formula

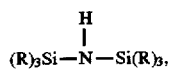

wherein the R groups are independently hydrocarbyl groups (preferably, $C_1$–$C_4$ alkyl) or hydrogen. Especially preferred for use are the hexaalkyl substituted disilazanes such as, for example, hexamethyidisilazane.

Treatment with the silylating agent may be performed either in the liquid phase (i.e., where the silylating agent is applied to the catalyst as a liquid, either by itself or as a solution in a suitable solvent such as a hydrocarbon) or in the vapor phase (i.e., where the silylating agent is contacted with the catalyst in the form of a gas). Treatment temperatures are preferably in the 100° C. to 450° C. range, with somewhat higher temperatures (e.g., 300° C. to 425° C.) being generally preferred wherein the silylating agent is an organohalosilane and somewhat lower temperatures (e.g., 100° C. to 300° C.) being preferred for the organosilazanes. The silylation may be carried out in a batch, semi-continuous, or continuous manner.

The length of time required for the silylating agent to react with the surface of the regenerated catalyst depends in part on the temperature and agent employed. Lower temperatures generally require longer reaction times. Generally, times of from 0.1 to 48 hours are suitable.

The amount of silylating agent employed can vary widely. Suitable amounts of silylating agent can range from about 1 percent by weight (based on the weight of the entire regenerated catalyst composition) to about 75 percent by weight, with amounts of from 2 to 50 percent by weight typically being preferred. The silylating agent can be applied to the regenerated catalyst either in one treatment or a series of treatments.

In one embodiment of the invention, the spent catalyst is contained in a suitable vessel as a fixed bed and subjected to both calcination and silylation in the same vessel. For example, the vessel is first heated to a temperature of 700° C. or higher while passing an oxygen-containing gas through the fixed bed. Once a satisfactory degree of reactivation is achieved, feed of the oxygen-containing gas is discontinued, the temperature is lowered to a temperature suitable for the silylation reaction (e.g., 100° C. to 450° C.), and the silylating agent introduced into one end of the vessel in the form of a gas and permitted to react with the catalyst surface while being passed through the fixed bed.

The reactivated catalyst may also be hydrated prior to silylation, preferably after calcination. Hydration is effected by contacting the catalyst with water and then heating it or by contacting the catalyst with steam at an elevated temperature (preferably, a temperature in excess of 100° C., more preferably, a temperature in the range of 150° C. to 450° C.) for from about 0.5 to 6 hours.

The regenerated catalyst which has been reactivated in accordance with the process of the invention may be admixed with freshly prepared catalyst prior to reuse, if so desired, or used directly.

EXAMPLES

Example 1

A titania-on-silica catalyst was prepared by the procedures described in U.S. Pat. No. 3,923,843. The catalyst thus obtained was synthetically deactivated by heating at 100° C. in an ethylbenzene solution of distillation bottoms recovered from a propylene oxide/styrene plant. The deactivated catalyst was recovered, washed twice with 300 mL of water on a filter bed, and portions of the washed catalyst calcined in air at temperatures ranging from 500° C. to 800° C. The calcined catalysts were then resilylated in a flow reactor at 200° C. using gaseous hexamethyldisilazane. This procedure was repeated omitting the water-washing step. Batch epoxidation of 1-octene was performed using ethyl benzene hydroperoxide (900° C., 1 hr.) to compare the performance of the catalyst treated under the varying conditions described hereinabove.

| Regeneration Temperature, °C. | Calcination Time, hr. | % EBHP Conversion | |
|---|---|---|---|
| | | Water-Wash | No Water-Wash |
| 500 | 21 | 32 | 40 |
| 600 | 12 | 50 | 45 |
| 700 | 6 | 66 | 57 |
| 800 | 3 | 69 | 62 |
| fresh catalyst | | 74 | |
| deactivated catalyst | | 7 | |

These results demonstrate the dependance of catalyst reactivation on calcination temperature. Exposure to high temperatures (i.e., at least 700° C.) is necessary in order to adequately restore catalytic performance. The beneficial effect of water washing is also evident.

Example 2

Portions of a deactivated catalyst prepared in the same manner as Example 1 were first heated at temperatures ranging from 400° C. to 800° C. in a nitrogen atmosphere, then exposed to a mixture of nitrogen and air containing 5% oxygen at the same temperature.

Batch epoxidation of 1-octene was performed using the treated catalysts under the same conditions as described in Example 1. Heating the deactivated catalyst at temperatures of 700° C. or higher resulted in higher catalyst activity than did treatment at lower temperatures, even with shorter regeneration times.

| Example | Regeneration Temp., °C. | Regeneration Time, hr ($N_2$) | Regeneration Time, hr (Air/$N_2$) | EBHP Conversion, % | Epoxide Selectivity, % |
|---|---|---|---|---|---|
| 2-A | 500 | 21 | 21 | 29 | 75 |
| 2-B | 600 | 12 | 12 | 32 | 80 |
| 2-C | 700 | 6 | 6 | 40 | 80 |
| 2-D | 800 | 3 | 3 | 44 | 80 |

Example 3

A deactivated silylated titania-on-silica catalyst prepared by the procedures of U.S. Pat. No. 3,923,843 was removed from a fixed bed propylene epoxidation reactor after approximately 160 hours on stream and regenerated in accordance with the process of this invention. The used catalyst was calcined at 725° C. in a flow reactor under an air/$N_2$ atmosphere containing about 5 volume % oxygen for 3 hours. The heated catalyst was then re-silylated at 200° C. under a flowing gaseous stream of hexamethyldisilazane. Catalyst regenerated in this matter exhibited an activity profile (as measured by hydroperoxide conversion) very similar to that of freshly prepared catalyst when used to catalyze the continuous epoxidation of propylene using ethyl benzene hydroperoxide in the aforementioned fixed bed reactor (12:1 propylene:EBHP, LHSV =7 $hr^{-1}$, set temp. range =60°–85° C., pressure =885 psig) over a 144 hour period.

Example 4

This example shows that the effectiveness of catalyst regeneration is largely independent of the calcination time, but is greatly affected by the calcination temperature. Portions of a deactivated silylated titania-on-silica catalyst were heated in air in a muffle furnace for varying periods of time at varying temperatures. The catalytic performances of the resulting products in the epoxidation of 1-octene were then evaluated (90° C., 1 hr.). The results obtained are shown in the following table.

| Example | Regeneration Temp., °C. | Regeneration Time, hr. | EBHP Conversion, % | Epoxide Selectivity, % |
|---|---|---|---|---|
| 4-A | 500 | 21 | 35 | 79 |
| 4-B | 500 | 36 | 32 | 88 |
| 4-C | 500 | 84 | 32 | 81 |
| 4-D | 600 | 12 | 41 | 78 |
| 4-E | 600 | 44 | 42 | 78 |
| 4-F | 700 | 6 | 46 | 77 |
| 4-G | 700 | 27 | 45 | 77 |
| 4-H | 800 | 3 | 50 | 81 |
| 4-I | 800 | 6 | 46 | 81 |
| 4-J | 800 | 27 | 52 | 82 |

We claim:

1. A method of regenerating a used non-zeolitic heterogeneous catalyst composition comprised of an oxygen compound of silicon in chemical combination with an inorganic compound of titanium and which has been used in an epoxidation process wherein an olefin is reacted with an organic hydroperoxide, said method comprising heating said used heterogeneous catalyst composition at a temperature of at least 700° C. in the presence of oxygen to produce a reactivated heterogeneous catalyst composition.

2. The method of claim 1 wherein the temperature is at least 800° C.

3. The method of claim 1 wherein the inorganic oxygen compound of silicon is silica.

4. The method of claim 1 comprising the additional step of washing the used non-zeolitic heterogeneous catalyst composition with a solvent prior to heating.

5. The method of claim 1 wherein the reactivated heterogeneous catalyst composition is silylated by treatment with an organic silylating agent.

6. The method of claim 1 wherein the inorganic oxygen compound of titanium is selected from the group consisting of titanium oxides, titanium hydroxides and mixtures thereof.

7. The method of claim 1 comprising an initial step wherein the used non-zeolitic heterogeneous catalyst composition is heated at a temperature of at least 700° C. in the absence of oxygen.

8. A method of regenerating a used non-zeolitic heterogeneous catalyst composition comprised of silica in chemical combination with an inorganic oxygen compound of titanium which has been used in an epoxidation process wherein an olefin is reacted with an organic hydroperoxide, said method comprising:

(a) heating said used non-zeolitic heterogeneous catalyst composition at a temperature of from 700° C. to 900° C. in the presence of a flowing gas stream comprised of oxygen to produce a reactivated non-zeolitic heterogeneous catalyst composition; and (b) reacting said reactivated non-zeolitic heterogeneous catalyst composition with an organic silylating agent to form a silylated activated non-zeolitic heterogeneous catalyst composition.

9. The method of claim 8 wherein the organic silylating agent is selected from the group consisting of organohalosilanes, organosilylamines, organosilazanes, and mixtures thereof.

10. The method of claim 8 comprising an additional step of washing the used non-zeolitic heterogeneous catalyst composition with a solvent selected from the group consisting of water and aliphatic alcohols prior to step (a).

11. The method of claim 8 wherein the organic silylating agent is an organodisilazane.

12. The method of claim 8 wherein the inorganic oxygen compound of titanium is selected from the group consisting of titanium oxides, titanium hydroxides, and mixtures thereof.

13. The method of claim 8 wherein air is used as the flowing gas stream.

14. The method of claim 8 comprising an initial step prior to step (a) wherein the used non-zeolitic heterogeneous catalyst composition is heated at a temperature of at least 700° C. in the absence of oxygen.

15. The method of claim 1 wherein the olefin contains from 3 to 10 carbon atoms and the organic hydroperoxide is selected from the group consisting of tertiary butyl hydroperoxide, tertiary amyl hydroperoxide, ethyl benzene hydroperoxide, cumene hydroperoxide, cyclohexyl hydroperoxide, and methylcyclohexyl hydroperoxide.

16. The method of claim 8 wherein the olefin is propylene and the organic hydroperoxide is ethyl benzene hydroperoxide.

* * * * *